US006332468B1

(12) United States Patent
Benetti

(10) Patent No.: US 6,332,468 B1
(45) Date of Patent: *Dec. 25, 2001

(54) METHOD FOR CORONARY ARTERY BYPASS

(75) Inventor: Frederico J. Benetti, Rosario-Santa Fe (AR)

(73) Assignee: Cardiothoracic Systems, Inc., Cupertino, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/390,821

(22) Filed: Sep. 7, 1999

Related U.S. Application Data

(62) Division of application No. 09/340,913, filed on Jun. 28, 1999, now Pat. No. 6,167,889, which is a continuation of application No. 08/889,616, filed on Jul. 7, 1997, now Pat. No. 5,947,125, which is a continuation of application No. 08/419,991, filed on Apr. 10, 1995, now Pat. No. 5,888,257.

(51) Int. Cl.[7] ................................................. A61B 1/19
(52) U.S. Cl. ....................................................... 128/898
(58) Field of Search ............................. 128/858; 604/4, 604/5, 49; 606/192, 194, 185, 7, 8; 600/201, 208, 213, 204, 205, 114, 128, 129, 130

(56) References Cited

U.S. PATENT DOCUMENTS

| 4,726,356 | 2/1988 | Santilli et al. |
| 4,852,552 | 8/1989 | Chaux |
| 5,025,779 | 6/1991 | Bugge |
| RE34,150 | 12/1992 | Santilli et al. |

(List continued on next page.)

FOREIGN PATENT DOCUMENTS

| 0293 760 B1 | 2/1995 | (EP) . |
| 2 267 827 A | 12/1993 | (GB) . |
| WO 93/09720 | 5/1993 | (WO) . |
| WO 94/18881 | 9/1994 | (WO) . |
| WO 95/01757 | 1/1995 | (WO) . |
| WO 95/15715 | 6/1995 | (WO) . |

OTHER PUBLICATIONS

Acuff et al. (1996) "Minimally Invasive Coronary Artery Bypass Grafting," Ann Thorac Surg, vol. 61, pp. 135–137.

Akins (1994) "Controversies in Myocardial Revascularization: Coronary Artery Surgery for Single–Vessel Disease," Seminars in Thoracic and Cardiovascular Surgery, vol. 6, No. 2 pp. 109–115.

Akins et al. (1983) "Reoperation for Stenotic Saphenous Vein Bypass Grafts Without Cardiopulmonary Bypass," The *Annals of Thoracic Surgery*, vol. 35, No. 2, pp. 201–206.

(List continued on next page.)

*Primary Examiner*—David J. Isabella
(74) *Attorney, Agent, or Firm*—Alan W. Cannon; Bozicevic, Field & Francis LLP

(57) ABSTRACT

Methods for performing a coronary artery bypass graft on a beating heart. Thoracoscopic visualization is used to view at least one of the steps of the procedure that include locating a target artery for an arterial blood supply; introducing instruments through one or more small openings in the patient's chest to prepare the target artery, and introducing instruments through one or more small openings in the patient's chest to connect the target artery with the coronary artery. At least one small opening is formed in the patient's chest, a target artery for an arterial blood supply is located instruments are introduced through one or more small openings formed in the patient's chest to prepare the target artery for fluid connection to the coronary artery, and instruments are introduced through one or more small openings formed in the patient chest to connect the target artery to the coronary artery distal from a stenosis.

4 Claims, 8 Drawing Sheets

U.S. PATENT DOCUMENTS

| | | |
|---|---|---|
| 5,370,685 | 12/1994 | Stevens |
| 5,429,144 | 7/1995 | Wilk |
| 5,433,700 | 7/1995 | Peters |
| 5,452,733 | 9/1995 | Sterman et al. |
| RE35,352 | 10/1996 | Peters |
| 5,571,215 | 11/1996 | Sterman et al. |
| 5,584,803 | 12/1996 | Stevens et al. |
| 5,613,937 | 3/1997 | Garrision et al. |
| 5,735,290 | 4/1998 | Sterman et al. |
| 5,789,661 | 8/1998 | Fauque et al. |
| 5,807,243 | 9/1998 | Vierra et al. |
| 5,888,247 * | 3/1999 | Benetti .............................. 128/898 |
| 5,924,424 | 7/1999 | Stevens et al. |
| 5,947,125 * | 9/1999 | Benetti .............................. 128/898 |
| 5,957,832 | 9/1999 | Taylor et al. |
| 5,961,481 | 10/1999 | Sterman et al. |
| 6,017,304 | 1/2000 | Vierra et al. |
| 6,027,476 | 2/2000 | Sterman et al. |
| 6,029,671 | 2/2000 | Stevens et al. |
| 6,139,492 | 10/2000 | Vierra et al. |
| 6,167,889 * | 1/2001 | Benetti .............................. 128/898 |

OTHER PUBLICATIONS

Akins et al. (1984) "Preservation of Interventricular Septal Function in Patients Having Coronary Artery Bypass Grafts Without Cardiopulmonary Bypass," American *Heart Journal*, vol. 107, No. 2, pp. 304–309.

Allori (1995) "Bypass Senza Spargimento di Sangue," Salve, N.2, pp. 38–42.

Ancalmo et al. (1976) "A Modified Sternal Retractor," The Annals of Thoracic Surgery. vol. 21, p. 174.

Archer et al. (1984) "Coronary Artery Revascularization Without Cardiopulmonary Bypass," *Texas Heart Institute Journal*, vol. 11(1), pp. 52–57.

Arsiwala et al. (1990) "Coronary Artery Bypass Grafting Without Cardiopulmonary Bypass," Indian Heart Journal, vol. 42, No. 6, pp. 453–454.

Baeza et al. (1976) "Vertical Axillary Thoracotomy: A Functional and Cosmetically Appealing Incision," The Annals of Thoracic Surgery, vol. 22, No. 3, pp. 287–288.

Becker et al. (1976) "Transaxillary Minithoracotomy: The Optimal Approach for Certain Pulmonary and Mediastinal Lesions," The Annals of Thoracic Surgery, vol. 22, No. 3, pp. 254–259.

Beg et al. (1985) "Internal Mammary Retractor," The Annals of Thoracic Surgery, vol. 39, No. 1, pp. 286–287.

Benetti (1985) "Direct Coronary Surgery with Saphenous Vein Bypass Without Either Cardiopulmonary Bypass or Cardiac Arrest," The Journal of Cardiovascular Surgery, vol. 26(3), pp. 217–222.

Benetti (1991) "Coronary Artery Bypass Without Extracorporeal Circulation Versus Percutaneous Transluminal Coronary Angioplasty: Comparison of Costs," The Journal of Thoracic and Cardiovascular Surgery, vol. 102, No. 5, pp. 802–803.

Benetti et al. (1986) "Anastomosis Mamariocoronaria Sin Circulacion Extracorporea," Prense Medica Argen., vol. 73, pp. 213–215.

Benetti et al. (1995) Coronary Revascularization with Arterial Conduits Via a Small Thoracotomy and Assisted by Thoracoscopy, Although Without Cardiopulmonary Bypass, Cor Europaeum, vol. 4(1), pp. 22–24.

Benetti, M.D et al. (1991) "Direct Myocardial Revascularization Without Extracorporeal Circulation," *Chest*, vol. 100(2), pp. 312–316.

Bonchek (1992) "Technical Considerations for Coronary Artery Bypass Without Cardioplegia," Journal of Cardiac Surgery, vol. 7, No. 4, pp. 333–341.

Borst (1978) "Leftsided Thoracotomy for Coronary Artery Reoperation," *Thoraxchirurgie Vaskulare Chirurgie*, vol. 26, pp. 95–97.

Borst et al. (1995) "Regional Cardiac Wall Immunobilization for Open Chest and Closed Chest Coronary Artery Bypass Grafting on the Beating Heart: The 'Octopus' Method," Circulation, vol. 92, No. 8, supplement I, 1–177.

Buffolo et al. (1985) "Direct Myocardial Revascularization Without Cardiopulmonary Bypass," *Thoraic. Cardiovasc. Surgeon*, vol. 33, pp. 26–29.

Bugge (1990) "A New Internal Mammary Artery Retractor," Thorac. Cardiovasc. Surgeon, vol. 38, pp. 316–317.

Burlingame et al. (1988) "Left Thoracotomy for Reoperative Coronary Bypass," *Journal of Thoracic Cardiovascular Surgery*, vol. 95, pp. 508–510.

Calafiore et al. (1994) "Composite Arterial Conduits for a Wider Arterial Myocardial Revascularization," Ann. Thorac. Surg., vol. 58, pp. 185–190.

Chaux et al. (1986) "A New Concept in Sternal Retraction: Applications for Internal Mammary Artery Dissection and Valve Replacement Surgery," Ann. Thorac. Surg, vol. 42, pp. 473–474.

Cheung et al. (1982) "An Alternative Approach to Isolated Circumflex Coronary Bypass Reoperations," *The Annals of Thoracic Surgery*, vol. 33, pp. 302–303.

Corso (1991) "Cardiopulmonary Bypass and Coronary Artery Bypass Graft," *Chest*, vol. 100(2):298–9.

Fanning, MD et al. (1993) "Reoperative Coronary Artery Bypass Grafting Without Cardiopulmonary Bypass," *The Annals of Thoracic Surgery*, vol. 55, No. 2, pp. 486–489.

Faro et al. (1982) "Left Thoracotomy for Reoperation for Coronary Revascularation," *The Journal of Thoracic and Cardiovascular Surgery*, vol. 84, pp. 453–455.

Favaloro, M. D. et al. (1970) "Direct Myocardial Revascularization by Saphenous Vein Graft," The Annals of Thoracic Surgery, vol. 10, No. 2, pp. 97–111.

Gandjbakheh et al. (1989) "Left Thoracotomy Approach for Coronary Artery Bypass Grafting in Patients with Pericardial Adhesions," *The Annals of Thoracic Surgery*, vol. 48, pp. 871–873.

Grinda et al. (1996) "Right Anterolateral Thoracotomy for Repair of Atrial Septal Defect," Ann Thorac Surg, vol. 62, pp. 175–178.

Grosner et al. (1990) "Left Thoracotomy Reoperation for Coronary Artery Disease," *Journal of Cardiac Surgery*, vol. 5, pp. 304–308.

Horii et al. (1993) "Two–Staged Repeat Myocardial Revascularization Through the Sternal Re–Entry and the Left Thoracotomy with Coronary Anastomosis Under the Beating Heart," (English Abstract Only Attached) Journal of the Japanese Association for Thoracic Surgery, vol. 41(9), pp. 1511–1514.

Kawase et al. (1993) "A Case of Treating Abrupt Closure Due to Post PTCA Dissection by Emergent CABG–Reoperation, Via Extracorporeal Circulatory Method Conducted with the Heart 'Beating'," (English Abstract Only Attached) Japanese Journal of Thoracic Surgery, vol. 46(6), pp. 512–515.

Kolessov, M. D. (1967) "Mammary Artery–Coronary Artery Anastomosis as Method of Treatment for Angina Pectoris," *Thoracic and Cardiovascular Surgery*, vol. 54(4), pp. 535–544.

Kyobu et al. (1993) "Coronary Artery Bypass Grafting Surgery Without Cardiopulmonary Bypass," (English Abstract Only Attached) Department of Thoracic and Cardiovascular Surgery, St. Mary's Hospital, Kurme, Japan, vol. 4(4), pp. 598–602.

Loop et al. (1986) "Influence of the Internal–Mammary–Artery Graft on 10–Year Survival and Other Cardiac Events," N. Eng. J. Med., vol. 3145, No. 1, pp. 1–6.

Lytle et al. (1992) "Coronary Artery Bypass Surgery," Current Problems in Surgery, vol. XXIX, No. 10, pp. 737–807.

Maddaus et al. (1992) "Coronary Artery Surgery Without Cardiopulmonary Bypass: Usefulness of the Surgical Blower–Humidifier," *Journal of Cardiac Surgery*, vol. 7, No. 4., pp. 348–350.

McKeown et al. (1981) "A Modified Sternal Retractor for Exposure of the Internal Mammary Artery," The Annals of Thoracic Surgery. vol. 32, p. 619.

Mitchell et al. (1976) "Simplified Lateral Chest Incision for Most Thoracotomies Other Than Sternotomy," The Annals of Thoracic Surgery, vol. 22, No. 3, pp. 284–286.

Moshkovitz et al. (1993) "Coronary Artery Bypass Without Cardiopulmonary Bypass—the Pros and the Cons," Isr J Med Sci, vol. 29, pp. 716–720.

Pfister, MD et al. (1992) "Coronary Artery Bypass Without Cardiopulmonary Bypass," *The Annals of Thoracic Surgery*, vol. 54, No. 6, pp. 1085–1092.

Richenbacher et al. (1989) "Current Status of Cardiac Surgery: A 40–Year Review," FACC Journal of the American College of Cardiology, vol. 14, No. 3, pp. 535–544.

Robinson et al. (1995) "A Minimally Invasive Surgical Method for Coronary Revascularization—Preliminary Experience in Five Patients," Circulation, vol. 92, No. 8,1–176.

Robinson et al. (1995) "Minimally Invasive Coronary Artery Bypass Grafting: A New Method Using an Anterior Mediastinotomy," *Journal of Cardiac Surgery*, vol. 10, pp. 529–536.

Schwartz et al. (1996) "Minimally Invasive Cardiopulmonary Bypass with Cardioplegic Arrest: A Closed Chest Technique with Equivalent Myocardial Protection," The Journal of Thoracic and Cardiovascular Surgery, vol. 111, No. 3, 556–66.

Stevens et al. (1994) "Closed–Chest Coronary Artery Bypass with Cardioplegic Arrest in the Dog," Circulation, vol. 90, No. 4, Part 2, pp. 1–251.

Tector et al. (1994) "Total Revascularization with T Grafts," Ann. Thorac. Surg., vol. 57, pp. 33–39.

Trapp et al. (1975) "To Use or Not To Use the Pump Oxygenator in Coronary Bypass Operations," *The Annals of Thoracic Surgery*, vol. 19, No. 1, pp. 108–109.

Trapp et al. (1975) "Placement of Coronary Artery Bypass Graft Without Pump Oxygenator," The Annals of thoracic Surgery, vol. 19, No. 1, pp. 1–9.

Ungerleider et al. (1985) "Left Thoracotomy for Reoperative Coronary Artery Bypass Procedures," *The Annals of Thoracic Surgery*, vol. 40, pp. 11–15.

Uppal et al. (1994) "Right Thoracotomy for Reoperative Right Coronary Artery Bypass Procedures," *The Annals of Thoracic Surgery*, vol. 57, pp. 123–125.

Vincent (1989) "A Compact Single Post Internal Mammary Artery Dissection Retractor," Eur.J.Cardiothorac Surg, vol. 3. pp. 276–277.

Walker et al. (1986) "Avoidance of Patent Anterior Grafts at Revisional Coronary Artery Surgery: Use of a Lateral Thoracotomy Approach," Thorax, vol. 41, pp. 692–695.

Weintraub et al. (1994) "The Impact of Additional Procedures on the Cost at Three Years of Coronary Angioplasty and Coronary Surgery in the EAST Trial," *Circulation*, vol. 90, No. 4, Part 2, pp. 1–91.

Westaby (1995) "Coronary Surgery Without Cardiopulmonary Bypass," Br Heart J., vol. 73(3):203–5.

"Mammary Artery–Coronary Artery Anastomosis as Method of Treatment for Angina Pectoris," V. I. Kolessov, M. D. *Thoracic and Cardiovascular Surgery*, vol. 54, No. 4, Oct., 1967, pp. 535–544.

"Direct Coronary Surgery with Saphenous Vein Bypass Without Either Cardiopulmonary Bypass or Cardiac Arrest," F. J. Benetti *The Journal of Cardiovascular Surgery*, vol. 26, No. 3, May–Jun., 1985, pp. 217–222.

"Direct Myocardial Revascularization Without Cardiopulmonary Bypass," E. Buffolo; J. C. S. Andrade; J.Succi; L. E. V. Leao, and C. Gallucci Thoac. Cardiovasc. Surgeon, 33 (1985) pp. 26–29.

"Coronary Artery Revascularization Without Cardiopulmonary Bypass," R. Archer, D. O.; D. A. Ott, M. D.; R. Parravicini, M. D.; D. A. Cooley, M. D.; G. J. Reul, M. D.; O. H. Frazier, M. D.; J. M. Duncan, M. D.; J. J. Livesay, M. D., and W. E. Walker, M. D. *Texas Heart Institute Journal*, vol. 11, No. 1, Mar. 1984, pp. 52–57.

"Direct Myocardial Revascularization Without Extracorporeal Circulation," F. J. Benetti, M. D.; G. Naselli, M. D.; M. Wood, M. D.; and L. Geffner, M. D. Chest, vol. 100, No. 2, Aug., 1991, pp. 312–316.

"Reoperative Coronary Artery Bypass Grafting Without Cardiopulmonary Bypass," W. J. Fanning, MD; G. S. Kakos, MD; and T. E. Williams, Jr., MD, PhD *The Annals of Thoracic Surgery*, vol. 55, No. 2, Feb. 1993, pp. 486–489.

"Coronary Artery Bypass Without Cardiopulmonary Bypass," A. J. Pfister, MD; M. S. Zaki, MD; J. M. Garcia, MD; L. A. Mispireta, MD; P. J. Corso, MD; A. G. Qazi, MD; S. W. Boyce, MD; T. R. Coughlin, Jr., MD; and P. Gurny, MD *The Annals of Thoracic Surgery*, vol. 54, No. 6, Dec. 1992, pp. 1085–1092.

"To Use or Not To Use the Pump Oxygenator in Coronary Bypass Operations," Drs. W. G. Trapp and R. Bisarya *The Annals of Thoracic Surgery*, vol. 19, No. 1, Jan., 1975, pp. 108–109.

"Direct Myocardial Revascularization by Saphenous Vein Graft," R. G. Favaloro, M. D.; D. B. Effler, M. D.; L. K. Groves, M. D.; W. G. Sheldon, M. D.; and F. M. Sones, Jr., M. D. *The Annals of Thoracic Surgery*, vol. 10, No. 2, Aug., 1970, pp. 97–111.

"Preservation of Interventricular Septal Function in Patients Having Coronary Artery Bypass Grafts Without Cardiopulmonary Bypass," C. W. Akins, M. D.; C. A. Boucher, M. D., and G. M. Pohost, M. D. *American Heart Journal*, vol. 107, No. 2, Feb., 1984, pp. 304–309.

"Left Thoracotomy Reoperation for Coronary Artery Disease," Grosner, G, Lajos TZ, Schimertz G, Bergsland J. *Journal of Cardiac Surgery*, 1990, vol. 5, pp. 304–308.

"Left Thoracotomy for Reoperation for Coronary Revascularation," Faro RS, Javid H, Najafi H., C. Serry *The Journal of Thoracic and Cardiovascular Surgery*, 1982, vol. 84, pp. 453–455.

"An Alternative Approach to Isolated Circumflex Coronary Bypas Reoperations," Cheung D, Flemma RJ, Mullen DC, Lepley D, Jr. *The Annals of Thoracic Surgery*, 1982, vol. 33, pp. 302–303.

"Left Thoracotomy for Reoperative Coronary Bypass," Burlingame, MW, Bonchek, LI, and Vazales, BE.; *Journal of Thoracic Cardiovascular Surgery*, 1988, vol. 95, pp. 508–510.

"Left Thoracotomy for Reoperative Coronary Artery Bypass Procedures," Ungerleider, RM, Mills NL, Wechsler, AS. *The Annals of Thoracic Surgery*, 1985, vol. 40, pp. 11–15.

"Leftsided Thoracotomy for Coronary Artery Reoperation," Borst HG. *Thoraxchirurgie Vaskulare Chirurgie*, 1978, vol. 26, pp. 95–97.

"Avoidance of Patent Anterior Grafts at Revisional Coronary Artery Surgery: Use of a Lateral Thoracotomy Approach," Walker, WS, Sang CTM; . *Thorax*, 1986, vol. 41, pp. 692–695.

*The Annals of Thoracic Surgery*, 1989, vol. 48, pp. 871–873.

"Right Thoracotomy for Reoperative Right Coronary Artery Bypass Procedures," Uppal R, Wolfe WG, Lowe JE, and Smith PK. *The Annals of Thoracic Surgery*, 1994, vol. 57, pp. 123–125.

"Reoperation for Stenotic Saphenous Vein Bypass Grafts Without Cardiopulmonary Bypass," Akins CA. *The Annals of Thoracic Surgery*, 1983, vol. 35, No. 2, pp. 201–206.

"Cardiopulmonary Bypass and Coronary Artery Bypass Graft," Corso PG. *Chest*, 1991, vol. 100.

"Coronary Artery Bypass Without Cardiopulmonary Bypass—the Pros and the Cons," Moshkovita Y, and Mohr R. *Isr J Med Sci*, 1993, vol. 29, pp. 716–720.

"Minimally Invasive Coronary Artery Bypass Grafting: A New Method Using an Anterior Mediastinotomy," MC Robinson, DR Gross, W Zeman, and E Stedje–Larsen. *Journal fo Cardiac Surgery*, 1995, vol. 10, pp. 529–536.

"Coronary Artery Surgery Without Cardiopulmonary Bypass: Usefulness of the Surgical Blower–Humidifier," Maddaus M, Ali I, Birnbaum P, Panos AL, and Salerno TA. *Journal of Cardiac Surgery*, 1992, vol. 7, No. 4.

"Technical Considerations for Coronary Artery Bypass Without Cardioplegia," Bonchek LI. *Journal of Cardiac Surgery*, 1992, vol. 7, No. 4, pp. 333–341.

"Coronary Artery Bypass Grafting Without Cardiopulmonary Bypass," Arsiwala S, Bedi HS, Sharma VK, and Trehan N. *Indian Heart Journal*, 1990, vol. 42, No. 6, pp. 453–454.

"Right Anterolateral Thoracotomy for Repair of Atrial Septal Defect," Grinda JM, Folliguet TA, Dervanian P, Mace L, Legault B, Neveux JY. *Ann Thorac Surg* 1996, vol. 62, pp. 175–178.

"Vertical Axillary Thoracotomy: A Functional and Cosmetically Appealing Incision," Baeza OR and Foster ED. *The Annals of Thoracic Surgery*, 1976, vol. 22, No. 3, pp. 287–288.

"Transaxillary Minithoracotomy: The Optimal Approach for Certain Pulmonary and Mediastinal Lesions," Becker RM and Munro DD. *The Annals of Thoracic Surgery*, 1976, vol. 22, No. 3, pp. 254–259.

"Simplified Lateral Chest Incision for Most Thoracotomies Other Than Sternotomy," Mitchell R, Angell W, Wuerflein R, and Dor V. *The Annals of Thoracic Surgery*, 1976, vol. 22, No. 3, pp. 284–286.

"Coronary Artery Bypass Without Extracorporeal Circulation Versus Percutaneous Transluminal Coronary Angioplasty: Comparison of Costs," Benetti FJ. *The Journal of Thoracic and Cardiovascular Surgery*, 1991, vol. 102, No. 5, pp. 802–803.

"Bypass Senza Spargimento di Sangue," Allori L. *Salve*, 1995, N.2, pp. 38–42.

"Coronary Artery Bypass Grafting Surgery Without Cardiopulmonary Bypass," Kyobu N, Zasshi GG. (English Abstract Only Attached) Department of Thoracic and Cardiovascular Surgery, St. Mary's Hospital, Kurme, Japan, 1993, vol. 4(4), pp. 598–602.

"A Case of Treating Abrupt Closure Due to Post PTCA Dissection by Emergent CABG–Reoperation, Via Extracorporeal Circulatory Method Conducted with the Heart 'Beating'," Kawase Y, Tanake N, Mukai K, Matsumoto Y, Kawasuji M, and Watanabe Y. (English Abstract Only Attached) *Japanese Journal of Thoracic Surgery*, 1993, vol. 46(6), pp. 512–515.

"Two–Staged Repeat Myocardial Revascularization Through the Sternal Re–Entry and the Left Thoracotomy with Coronary Anastomosis Under the Beating Heart," Horii T, Suma H, Wanibuchi Y, Fukuda S, Kigawa I. (English Abstract Only Attached) *Journal of the Japanese Association for Thoracic Surgery*, 1993, vol. 41(9), pp. 1511–1514.

"Current Status of Cardiac Surgery: A 40–Year Review," W. E. Richenbacher, MD; J. L. Myers, MD, FACC; J. A. Waldhausen, MD, FACC *Journal of the American College of Cardiology*, vol. 14, No. 3, Sep. 1989, pp. 535–544.

"The Impact of Additional Procedures on the Cost at Three Years of Coronary Angioplasty and Coronary Surgery in the EAST Trial," WS Weintraub, PD Mauldin, E Becker, and SB King III *Circulation*, vol. 90, No. 4, Part 2, Oct. 1994, pp. I–91.

"Closed–Chest Coronary Artery Bypass with Cardioplegic Arrest in the Dog," JH Stevens, LC Siegel, RS Mitchell, TA Burdon, GH Ribakove, JA SMith, FG St. Goar, WS Peters, MA Vierra, MF Pompili, and BA Reitz *Circualtion*, vol. 90, No. 4, Part 2, Oct. 1994, pp. I–251.

"Placement of Coronary Artery Bypass Graft Without Pump Oxygenator," WG. Trapp and R Bisarya *The Annals of thoracic Surgery*, (Jan. 1975) vol. 19, No. 1, pp. 1–9.

"Coronary Artery Bypass Surgery," BW. Lytle and DM Cosgrove III *Current Problems in Surgery*, (Oct. 1992), vol. XXIX, No. 10, pp. 737–807.

"Minimally Invasive Coronry Artery Bypass Grafting," TE Acuff, RJ Landreneau, BP Griffith, and MJ Mack *Ann Thorac Surg* (1996), vol. 61, pp. 135–137.

"Minimally Invasive Cardiopulmonary Bypass with Cardioplegic Arrest: A Closed Chest Technique with Equivalent Myocardial Protection," DS Schwartz; GH Ribakove, EA Grossi, JH Stevens, LC Siegel, FG St. Goar, WS Peters, D McLoughlin, FG Baumann, SB Colvin, and AC Galloway *The Journal of Thoracic and Cardiovascualr Surgery*, (1996) vol. 111, No. 3.

"Coronary Surgery Without Cardiopulmonary Bypass," S Westaby *The Heart Journal*, (Mar. 1995).

Coronary Revascularization with Arterial Conduits Via a Small Thoracotomy and Assisted by Thoracoscopy, Although Without Cardiopulmonary Bypass, FJ Benetti and C Ballester *Cor Europaeum*, (1995) vol. 4(1), pp. 22–24.

"Controversies in Myocardial Revascularization: Coronary Artery Surgery for Single–Vessel Disease," CW Akins *Seminars in Thoracic and Cardiovascular Surgery*, (Apr. 1994) vol. 6, No. 2, pp. 109–115.

"A Minimally Invasive Surgical Method for Coronary Revascularization—Preliminary Experience in Five Patients," MC Robinson, DR Gross, and W Zeman *Circulation*, (Oct. 15, 1995) vol. 92, No. 8, I–176.

"Regional Cardiac Wall Immunobilization for Open Chest and Closed Chest Coronary Artery Bypass Grafting on the Beating Heart: The 'Octopus' Method," C Borst, EWL Jansen, PF Grundemann, JWF van Dongen, HJ Mansvel Beck, H Wesenhagen, PJ Slootweg, JJ Bredee *Circulation*, (Oct. 15, 1995) vol. 92, No. 8 supplement I, I–177.

"Influence of the Internal–Mammary–Artery Graft on 10–Year Survival and Other Cardiac Events," FD Loop, B.W. Lytle, DMCosgrove, et al. *N. Eng. J. Med.*, 1986, vol. 3145, No. 1, pp. 1–6.

"Composite Arterial Conduits for a Wider Arterial Myocardial Revascularization,"AM Calafiore, GD Giammarco, N Luciani, et al. *Ann. Thorac. Surg.*, 1994, vol. 58, pp. 185–190.

"Total Revascularization with T Grafts," AJ Tector, S Amundsen, TM Schmahl, et al. *Ann. Thorac. Surg.*, 1994, vol. 57, pp. 33–39.

"Anastomosis Mamariocoronaria Sin Circulacion Extracorporea," FJ Benetti, J Rizzardi, R Aun, et al. *Prense Medica Argen.*, 1986, vol. 73, pp. 213–215.

"A New Internal Mammary Artery Retractor," M. Bugge *Thorac. Cardiovasc. Surgeon*, vol. 38, 1990, pp. 316–317.

"Internal Mammary Retractor," RA Beg, H Naraghipour, EB Kay, and P Rullo *The Annals of Thoracic Surgery*, vol. 39, No. 1, Jan. 1985, pp. 286–287.

"A New Concept in Sternal Retraction: Applications for Internal Mammary Artery Dissection and Valve Replacement Surgery," A Chaux and C Blanche *Ann. Thorac. Surg.*, vol. 42, Oct. 1986, pp. 473–474.

"A Compact Single Post Internal Mammary Artery Dissection Retractor," JG Vincent *Eur. J. Cardiothorac Surg.*, 1989, vol. 3, pp. 276–277.

"A Modified Sternal Retractor," N Ancalmo and JL Ochsner *The Annals of Thoracic Surgery*, vol. 21, Jan.–Jun. 1976, pp. 174.

"A Modified Sternal Retractor for Exposure of the Internal Mammary Artery," PP McKeown, J Crew, ES Hanna, and R Jones *The Annals of Thoracic Surgery*, vol. 32, Jul.–Dec. 1981, pp. 619.

* cited by examiner

METHOD FOR CORONARY ARTERY BYPASS

RELATED INFORMATION

This is a divisional of application Ser. No. 09/340,913 filed on Jun. 28, 1999, now U.S. Pat. No. 6,167,889, which is a continuation of application Ser. No. 08/889,616 filed on Jul. 7, 1997, now U.S. Pat. No. 5,947,125, which is a continuation of application Ser. No. 08/419,991 filed on Apr. 10, 1995, now U.S. Pat. No. 5,888,257.

BACKGROUND OF THE INVENTION

This invention is directed to a method for performing a minimally invasive coronary artery bypass graft. More particularly, the method permits a thoracoscopic procedure without the need for extracorporeal circulation or other cardiopulmonary bypass.

A coronary artery bypass graft (CABG) involves performing an anastomosis on a diseased coronary artery to reestablish blood flow to an ischemic portion of the heart muscle. Improved long-term survival has been demonstrated bypassing the left anterior descending artery (LAD) with a left internal mammary artery (LIMA). Loop, F. D., Lytle, B. W., Cosgrove, D. M., et al. "Influence of the Internal Mammary Artery on 10 Years Survival and Other Cardiac Events," *N. Eng. J. Med.*, 1986; 314:1–6. This has encouraged surgeons to extend revascularization with arterial grafts to all coronary arteries. In multiple-vessel disease, other arteries have then to be used, such as: the right internal mammary artery (RIMA), the right gastroepiploic artery, the inferior epigastric artery and the radial artery. At the same time, other techniques are also being used: arterial sequential anastomosis and/or graft elongated and/or Y- or T-grafts. Calafiore, A. M., DiGiamnarco, G., Luciani, N., et al. "Composite Arterial Conduits for a Wider Arterial Myocardial Revascularization." *Ann Thorac. Surg.*, 1994:58:185–191 and Tector, A. J., Amundson, S., Schmahl, T. M., et al. "Total Revasculization With T-Grafts". *Ann Thorac. Surg.*, 1994:57:33–39.

Traditionally, bypass graft procedures have required opening the chest wall via a sternotomy, stopping the heart and supporting the patient with a cardiopulmonary bypass system. These requirements are extremely invasive, pose significant risks, require lengthy hospitalization and are expensive. In hope of overcoming these and other problems, physicians have developed a number of alternatives such as percutaneous transluminal coronary angioplasty (PTCA), atherectomy, placement of stents and pharmacological treatments. The most common of these is PTCA which offers relatively short hospitalization periods and is relatively inexpensive. However, these benefits are mitigated by a significant restenosis rate. Similarly, the other alternatives suffer from their own drawbacks.

For these and other reasons, providing an anastomosis between an internal mammary artery and the LAD may be the best therapeutic option for severe proximal lesions. Benetti, F. J., Rizzardi, J. L., Naselli, G., et al., "Anastomosis Manerio Coronaria Sin Circulatión Extracorpórea," *Prense Médica Argentina*, 1985; 73:213. Accordingly, there is a need for improved CABG procedures that simplify surgical techniques and diminish hospital stays and costs.

SUMMARY OF THE INVENTION

The invention comprises a method for performing CABG procedures without the need for opening the chest wall, stopping the heart or providing cardiopulmonary bypass. Generally, at least one small opening is formed in the patient's chest, a target artery for an arterial blood supply is located through an opening in the patient's chest, instruments are introduced through one or more small openings formed in the patient's chest to separate the target artery from its support base; and instruments are introduced through one or more small openings formed in the patient's chest to connect the target artery to a portion of a coronary artery distal from a stenosis in fluid communication therewith to supply arterial blood from the target artery thereto. In a preferred embodiment, a minimal left anterior intercostal thoracotomy provides access to form the anastomosis between the left internal mammary artery (LIMA) and the left anterior descending artery (LAD) while thoracoscopic viewing facilitates harvesting the LIMA. In other embodiments, access to the patient's heart may be obtained through a trocar sheath or other means for providing percutaneous access to the patient's thoracic cavity without opening the chest wall. Depending on the type of access, thoracoscopic visualization is used to locate the arterial blood supply, the location of the coronary artery to be bypassed or the location of the occlusion in the artery. In other embodiments, the diagonal (Dx) or circumflex (Cx) arteries may be bypassed.

DETAILED DESCRIPTION OF THE DRAWINGS

In selected cases, it may be possible to avoid the risks of sternotomy and cardiopulmonary bypass, and obtain the benefits of arterial conduits. The patient is intubated with a double-lumen endobronchial tube (not shown) that allows selective ventilation or deflation of the right and left lungs. The left lung is deflated to provide access to the heart and the LIMA. The preferred surgical position of the patient is right lateral decubitus, 30 degrees from horizontal, with the left arm above the head.

Figure 1:
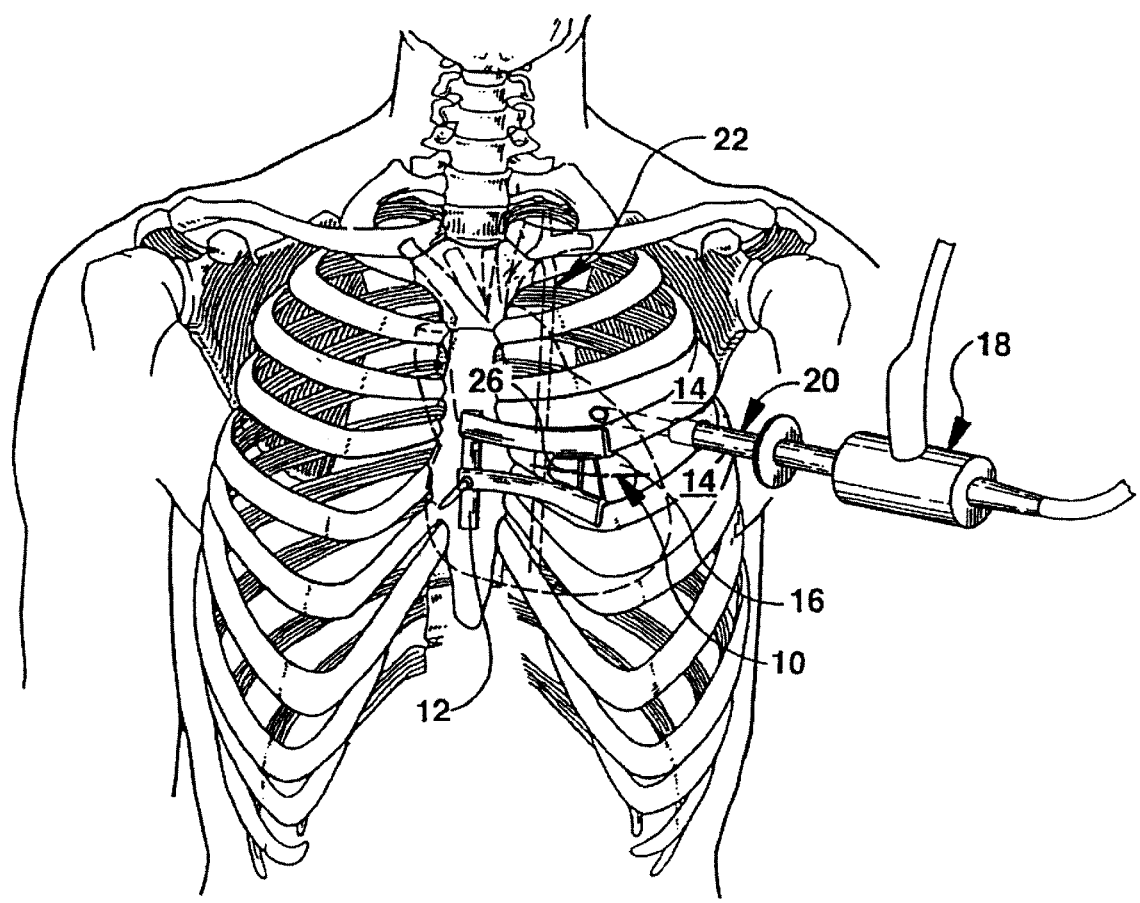
FIG. 1 is a schematic view showing placement of a thoracoscope and formation of a thoracotomy.
Figure 2:
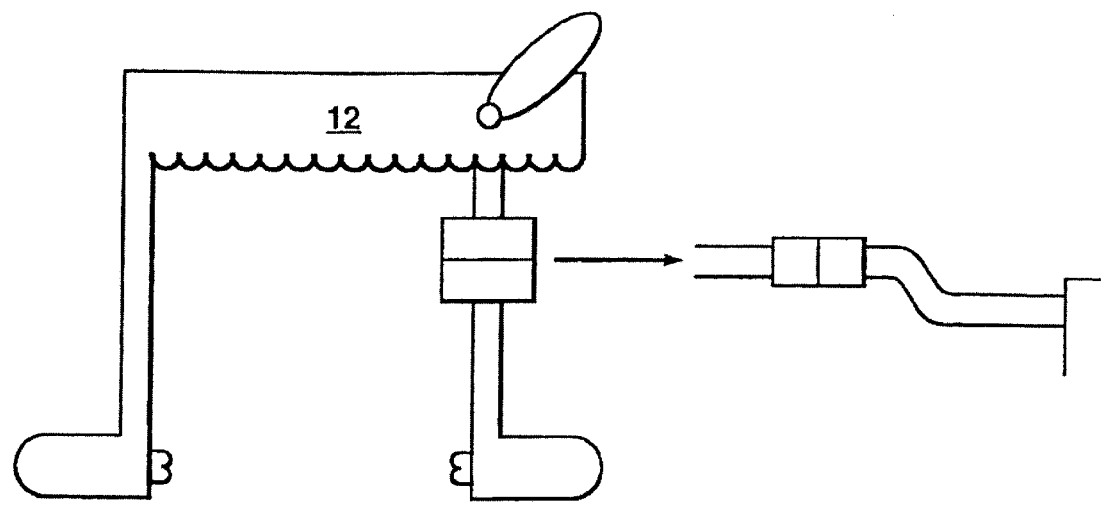
FIG. 2 is an elevational view of a retractor useful in the practice of the invention.
Figure 2:
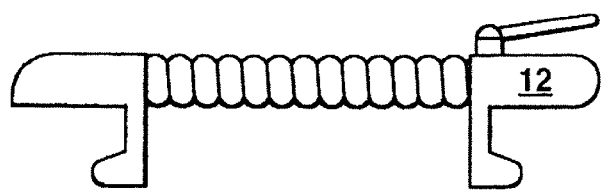
Figure 3:
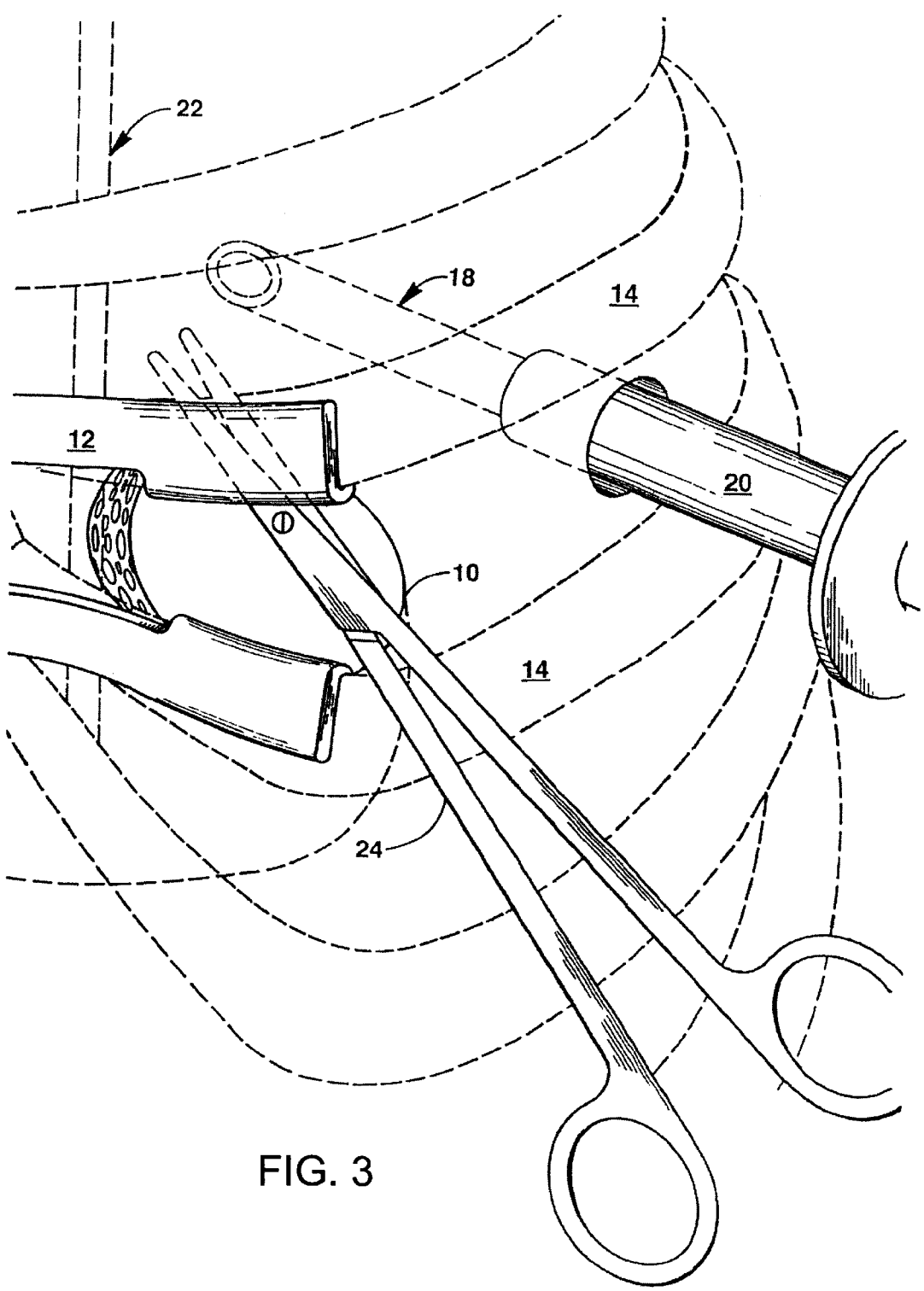
FIG. 3 is a schematic view showing dissection of the LIMA with instruments introduced through the thoracotomy.
Figure 4:
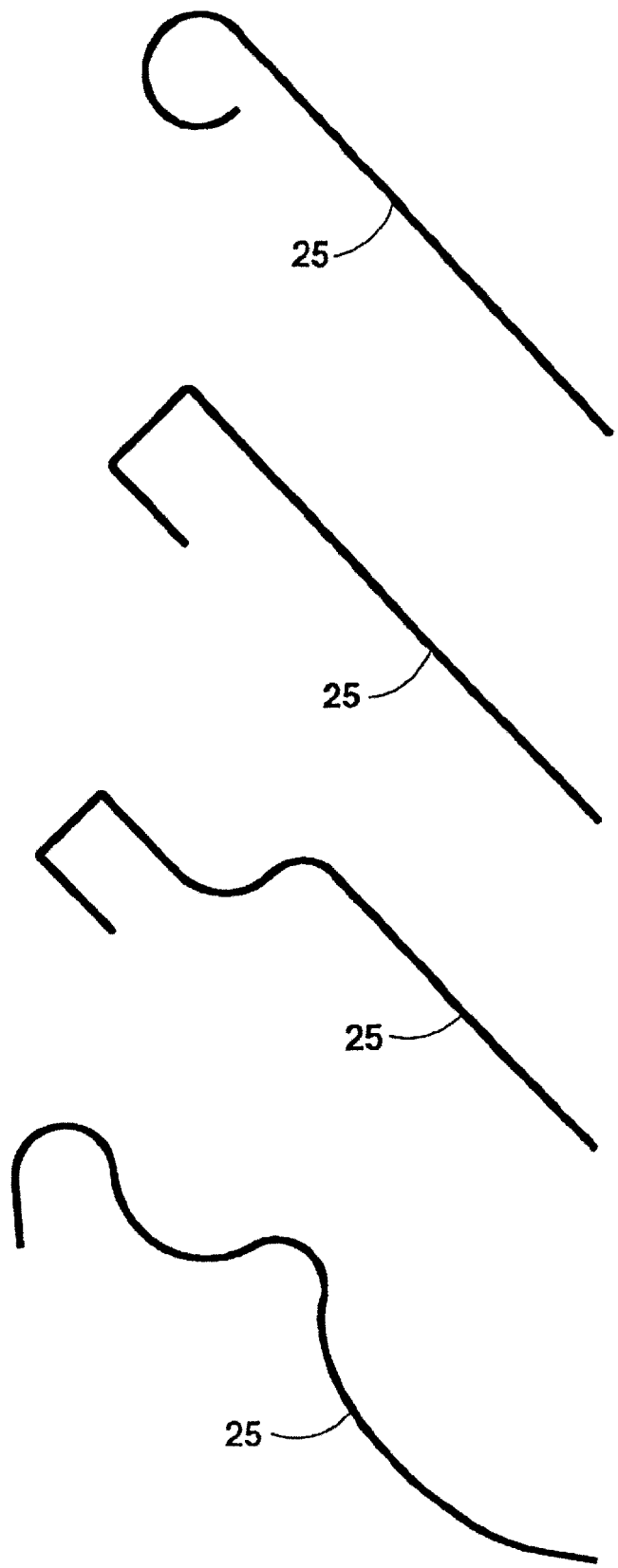
FIG. 4 shows various electrocauteries useful for dissecting the mammary artery.

Referring to FIG. 1, surgery begins with a left anterior thoracotomy 10 over the 4th intercostal space. Other sites are suitable depending on the patient's physiology, particularly the 5th intercostal space. Retractor 12 spreads ribs 14 to provide access to beating heart 16. FIG. 2 shows a special small retractor 12 which can spread the chest both horizontally and vertically. The size of thoracotomy 10 varies depending on the patient, but generally is less than 12 cm. The parietal pleura is dissected and separated from the ribbons, trying to keep it closed, to permit the introduction of thoracoscope 18 through trocar 20 at the 4th intercostal space, medial axillary line. The thoracoscope may be introduced through other areas such as the 5th through 7th intercostal spaces, again depending on the patients physiology. Thoracoscope 18 is positioned to provide visualization of the LIMA 22. As shown in FIG. 3, instrument 24 is introduced through thoracotomy 10 to dissect LIMA 22. Instrument 24 generally comprises scissors, clip appliers, electrocauteries and other conventional devices useful for the dissection. FIG. 4 shows a variety of electrocauteries 25 useful in the practice of the invention. In some embodiments, it is useful to make a graft with a radial artery coming out from the LIMA in a T-form. This allows the formation of anastomoses with multiple coronary arteries such as sequential grafts to the Dx and Cx arteries.

Following dissection of the LIMA 22, a small pericardial incision is made to expose LAD 26. Access to the LAD and Dx arteries is relatively easy, requiring an incision of about 5 cm. Access to the Cx artery depends on the patient's characteristics and location of the vessels. In some cases, a graft to the Cx artery requires increased rotation of the patent to the right lateral decubitus and some extension of the pericardial incision. Heparin, or other suitable anticoagulant, may be administered to the patient in an appropriate dose such as 1.5 mg/kg.

Figure 5:
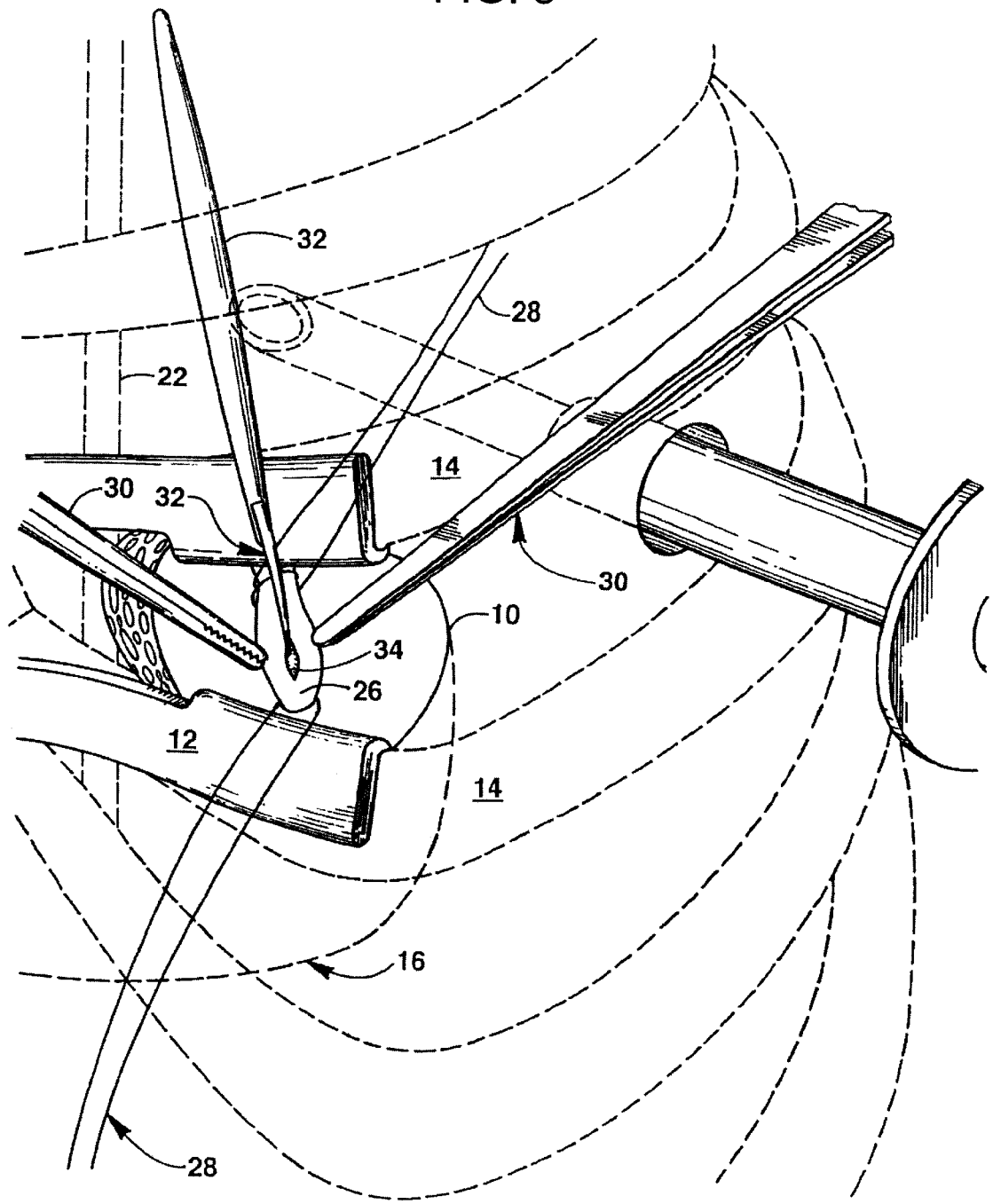
FIG. 5 is a schematic view showing instruments used to make an arteriotomy in the LAD introduced through the thoracotomy.
Figure 6:
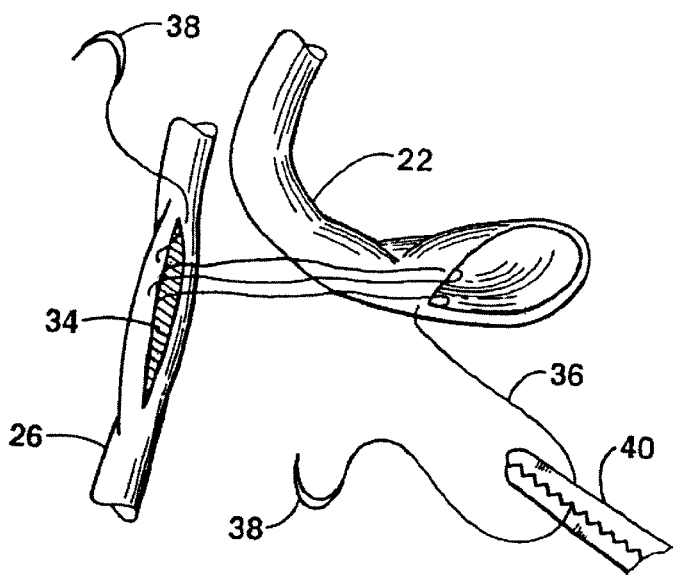
FIGS. 6–10 show the formation of the arteriectomy and the suturing of the LIMA to the LAD to provide an anastomosis.
Figure 7:
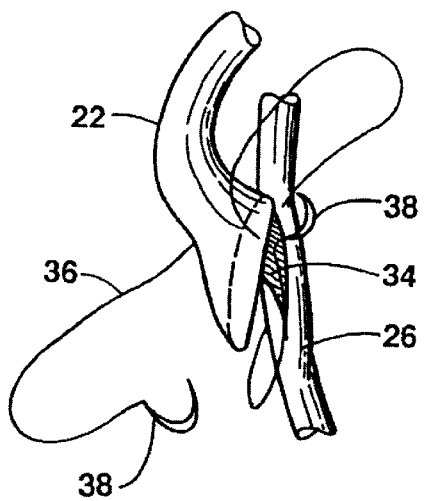
Figure 8:
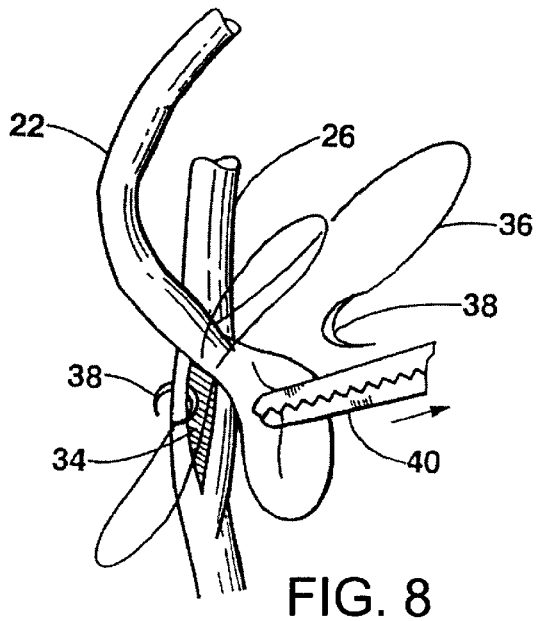
Figure 9:
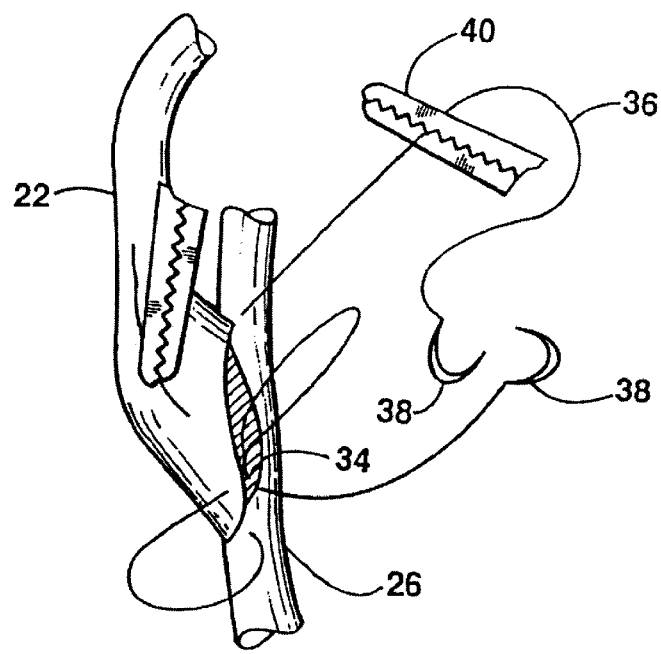
Figure 10:
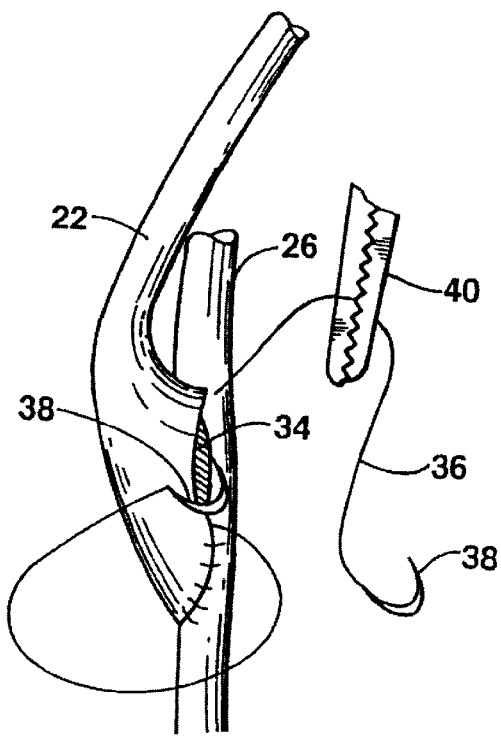

To prevent excess bleeding and to partially stabilize the vessel, a segment of LAD 26 is occluded with ligating stay sutures comprising 2.5 cm lengths of 5/0 polypropylene 28 or other appropriate ligature material as shown in FIG. 5. Applying tension to the ligatures 28 helps stabilize LAD 26 even though heart 16 is beating. Other conventional means for occluding and stabilizing the artery may be suitable. Forceps 30 are introduced through thoracotomy 10 to further stabilize and retract LAD 26. Scalpel 32 is then introduced to form arteriotomy 34 in LAD 26. As shown in FIGS. 6–10, the anastomosis between LIMA 22 and LAD 26 is formed by suturing with 7/0 polypropylene 36 and needle 38 manipulated by forceps 40. Other conventional means may be used as well. Preferably, the anastomosis is formed with a continuous suture and the aid of a conventional blower device (not shown). Further details of the blower are discussed in Tech K.H.T., Panos, A. L., Harmantas, A. A., et al. "Optimal Visualization of Coronary Artery Anastomosis by Gas Jet," *Ann, Thorac. Surg.*, 1991.

Upon completion of the anastomosis, the anticoagulant is reversed by suitable means such as prolamine. The hemostasis should be carefully controlled. The thoracotomy is closed in by conventional means; the surgery does not require resection of the costal cartilage. If the pleura is closed, a small tube for drainage may be left in place and removed the same day as surgery. If the pleura is open, a larger tube should be left in place for 24 hours. All drainage tubes are introduced through the small incision for the thoracoscope.

Figure 11:
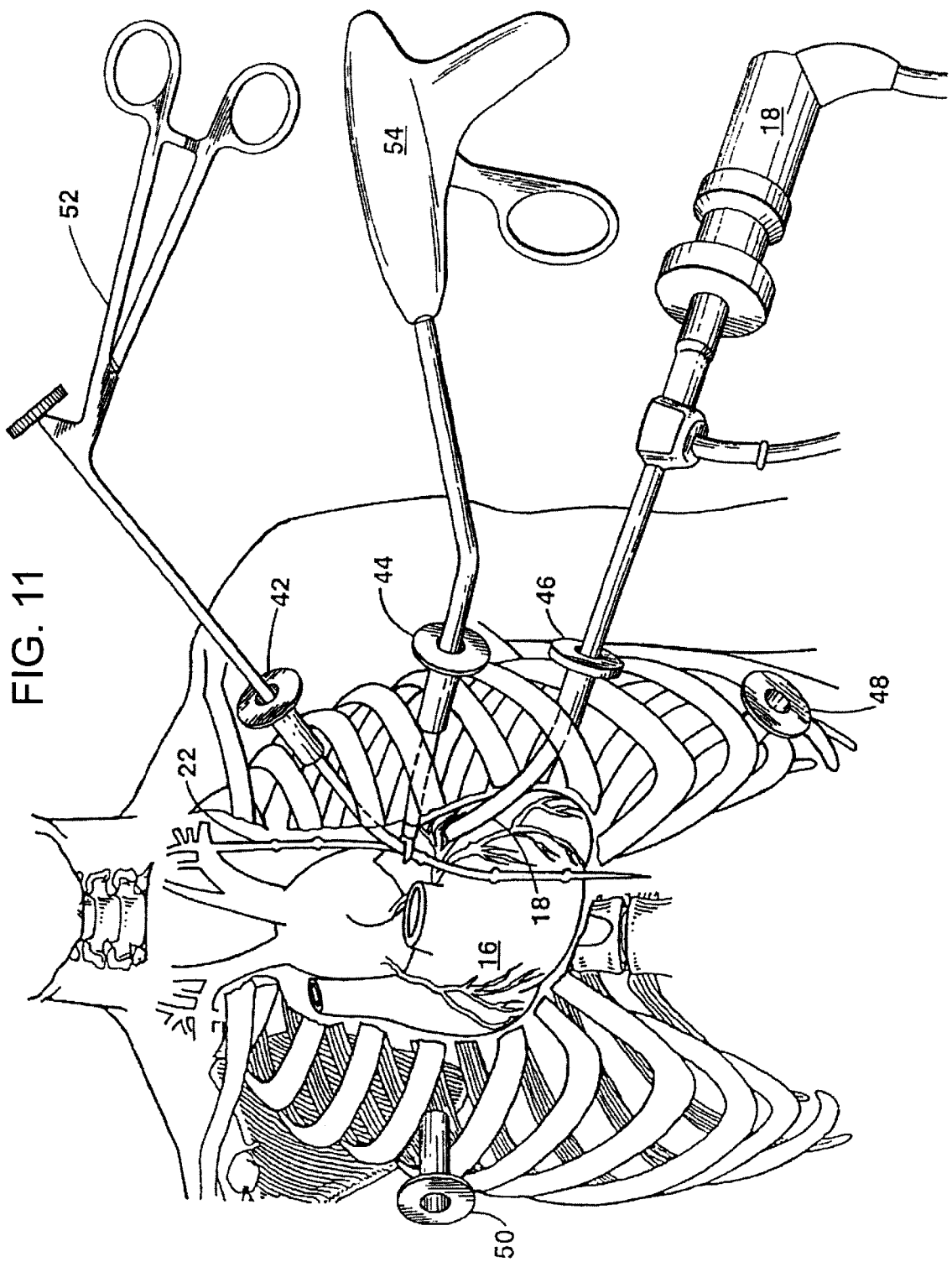
FIG. 11 is a schematic view of instruments for performing the bypass introduced through trocars without a thoracotomy.

FIG. 11 shows a series of trocars 42, 44, 46, 48 and 50 useful in the practice of the invention. In this embodiment, a thoracotomy is not necessary. Instruments 52 and 54 are introduced through the trocars to perform the dissection of the LIMA, the arteriotomy of the LAD and the formation of the anastomosis. Instruments 52 and 54 are conventional and include electrosurgical tools, graspers, forceps, scalpels, electrocauteries, clip appliers, scissors, etc. Although the trocars shown are introduced through the intercostal spaces, other points of access to the thorax may be suitable, such as parastemal punctures, midclavicular line punctures and a subxyphoid puncture.

EXAMPLES

The method of this invention was used to revascularize 10 patients from May to November 1994, one of them being a reoperation (a previous saphenous graft to LAD 11 years before). Sex was male/female in a proportion of 9/1. Age varied from 53 to 74, with an average of 61. Seven patients presented unstable angina, the other 3 suffering from stable angina. Pulmonary function was good in 8 patients, moderate in 1 and severely affected in 1. Four had previous myocardial infarction in other territories.

Access to the heart was through a small thoracotomy over the fifth left intercostal space and a thoracoscope was introduced through the fifth through seventh left intercostal space, medial axillary line, depending on the configuration of the patient's thorax. Eight patients were bypassed with a LIMA graft to LAD, the other two received triple grafts: LIMA to LAD plus a T-graft with radial artery, from the LIMA sequentially to the Dx and Cx arteries.

Mortality, morbidity and perioperative myocardial infarction have been 0% Six patients were extubated at the operating room. In 5, the pleura was maintained closed. Two patients were discharged from hospital 24 to 36 hours post-surgery; six patients were discharged between 36 and 72 hours; the other 2 were discharged 5 and 6 days post-surgery due to longer recovery time (both were patients with previous acute myocardial infarcts.) No blood transfusions were required. A new coronary angiography was done in 4 patients to monitor the patency of the grafts. Patency of the mammary artery graft was 100% when the patient was restudied before hospital discharge.

The drawings and examples are primarily directed to a graft involving the LIMA and the LAD, the Dx and the Cx arteries; nevertheless, this invention is suitable for many other graft possibilities. For example, other coronary arteries that may be bypassed include the obtuse marginal, the ramus intermedius, the right coronary, the posterior descending and others. Arteries other than the LIMA may be used to provide the arterial blood supply, such as the right internal mammary artery, the gastroepiploic artery and other arteries. Using a free graft shunt using a harvested vein or artery or a synthetic graft to form anastomoses between the aorta and the target coronary artery is also possible. Although intercostal thoracotomies are described to provide access to the heart, in some situations it may be desirable to remove a portion of a rib to improve access. Additionally, the methods of this invention can also be practiced with the use of extracoiporeal circulation, making a femoro-femoral cannulation (even percutaneously) to assist the patient for a few minutes during the anastomosis. These and other modifications that would be apparent to one skilled in the art are within the scope of this invention, which is to be limited only by the claims.

What is claimed is:

1. A method for performing a coronary artery bypass graft on a patient's beating heart comprising the steps of:
   a) forming at least one opening in the patient's chest,
   b) percutaneously introducing a viewing means through the patient's chest;
   c) locating a target artery for an arterial blood supply;
   d) introducing instruments through one or more small openings formed in the patient's chest to prepare the target artery for fluid connection to a portion of a coronary artery distal from a stenosis;
   e) introducing instruments through one or more small openings formed in the patient's chest to connect the target artery with the coronary artery and thereby supply arterial blood from the target artery to the coronary artery; and
   f) viewing at least one of steps c), d) and e) with the viewing means.

2. The method of claim 1 wherein the step of connecting the target artery in fluid communication with the coronary artery comprises forming an anastomosis between the target artery and the coronary artery.

3. The method of claim 1 wherein the step of connecting the target artery in fluid communication with the coronary artery comprises supplying a free graft means having first and second ends, forming a first anastomosis between the first end of the graft means and the target artery, and forming a second anastomosis between the second end of the graft means and the coronary artery.

4. The method of claim 1 further comprising the step of stabilizing the coronary artery before connecting the target artery thereto.

* * * * *

UNITED STATES PATENT AND TRADEMARK OFFICE
CERTIFICATE OF CORRECTION

PATENT NO.    : 6,332,468 B1
DATED         : December 25, 2001
INVENTOR(S)   : Benetti, Federico J., et al.

It is certified that error appears in the above-identified patent and that said Letters Patent is hereby corrected as shown below:

Column 2,
Line 50 "stemotomy" with -- sternotomy --.

Column 3,
Line 62 "parastemal" with -- parasternal --.

Column 4,
Line 43 "extracoiporeal" with -- extracorporeal --.

Signed and Sealed this

Twenty-first Day of May, 2002

Attest:

Attesting Officer

JAMES E. ROGAN
Director of the United States Patent and Trademark Office